United States Patent
Schnell et al.

(10) Patent No.: US 7,256,035 B1
(45) Date of Patent: Aug. 14, 2007

(54) SYSTEM FOR THERMOCYCLING OF FLUIDS IN CARTRIDGES

(75) Inventors: Urban Schnell, Müntschemier (CH); Olivier Elsenhans, Sins (CH); Thomas Caratsch, Mettmenstetten (CH); Lukas Birrer, Meggen (CH); Emad Sarofim, Hagendorn (CH)

(73) Assignee: Roche Molecular Systems, Inc, Alameda, CA (US)

( * ) Notice: Subject to any disclaimer, the term of this patent is extended or adjusted under 35 U.S.C. 154(b) by 682 days.

(21) Appl. No.: 10/070,343

(22) PCT Filed: Sep. 2, 2000

(86) PCT No.: PCT/EP00/08587

§ 371 (c)(1),
(2), (4) Date: Aug. 14, 2002

(87) PCT Pub. No.: WO01/17683

PCT Pub. Date: Mar. 15, 2001

(30) Foreign Application Priority Data

Sep. 4, 1999 (EP) .................................. 99117506

(51) Int. Cl.
*C12M 1/34* (2006.01)

(52) U.S. Cl. ................ 435/287.2; 435/288.3; 435/288.7; 435/293.1; 422/102; 356/246

(58) Field of Classification Search .............. 435/6, 435/91.2, 287.2, 288.7, 303.1; 422/68.1, 422/102, 82.09; 356/246
See application file for complete search history.

(56) References Cited

U.S. PATENT DOCUMENTS

| 5,567,617 | A | 10/1996 | Caprio et al. |
| 5,856,174 | A | 1/1999 | Lipshutz et al. |
| 6,071,394 | A * | 6/2000 | Cheng et al. ............... 204/547 |
| 6,087,182 | A | 7/2000 | Jeng et al. |
| 6,391,541 | B1 * | 5/2002 | Petersen et al. ............... 435/5 |

FOREIGN PATENT DOCUMENTS

| EP | 0 318 255 | 11/1988 |
| EP | 0 580 362 A1 | 7/1993 |
| EP | 0 640 828 A1 | 8/1994 |
| EP | 0 723 812 A1 | 1/1996 |
| WO | WO 96/41864 | 12/1996 |
| WO | WO 98/38487 | 9/1998 |

* cited by examiner

*Primary Examiner*—William H Beisner
(74) *Attorney, Agent, or Firm*—Townsend and Townsend and Crew, LLP; Charles M. Doyle

(57) ABSTRACT

System for thermocycling of fluids in cartridges comprising a thermocycling unit in thermal contact with a first substantially planar and heat conducting wall of a cartridge, a light source for transmitting light into the interior of said cartridge through a second light transparent wall of said cartridge which is arranged substantially perpendicular to said first wall, a light detector for detecting light emerging from the interior of the cartridge through said second wall and a fluid providing unit coupled to an inlet of the cartridge for providing the cartridge with fluid and an outlet of the cartridge to drain gas when the cartridge is filled with fluid. The invention further concerns a cartridge for conducting the thermal cycling of fluids.

24 Claims, 5 Drawing Sheets

SYSTEM FOR THERMOCYCLING OF FLUIDS IN CARTRIDGES

Figure 1:
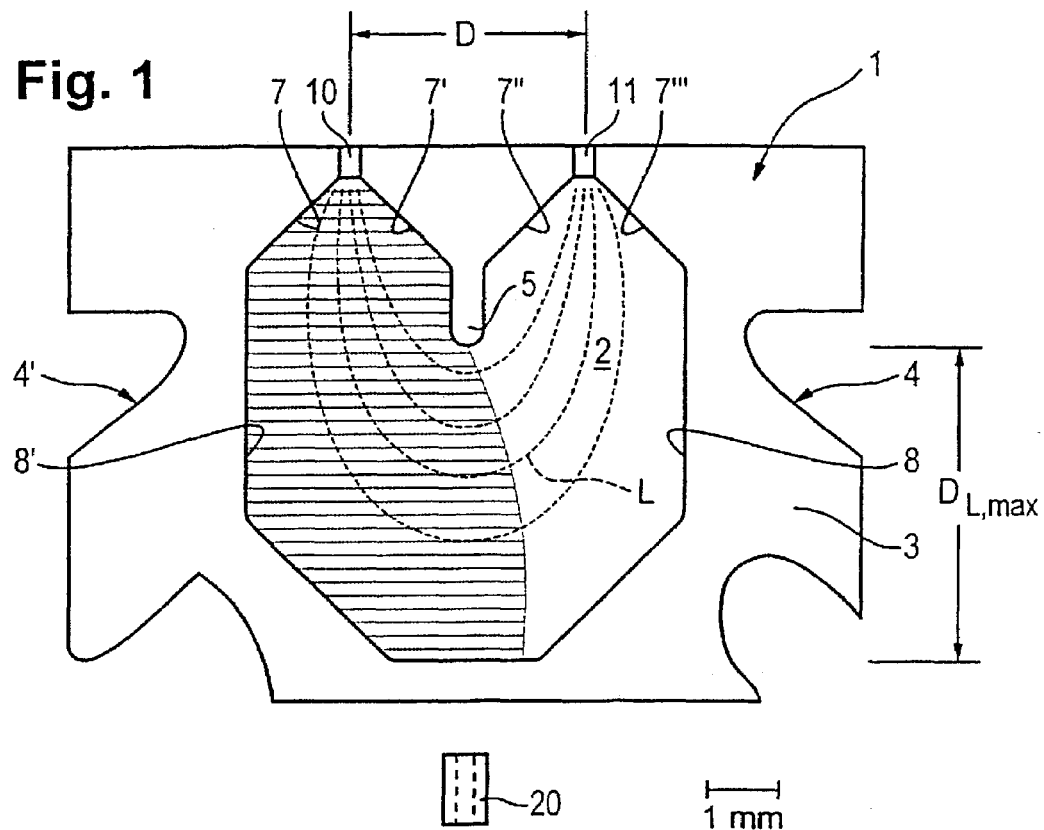

This invention is directed to a system for thermocycling fluids in cartridges to achieve an amplification and detection of nucleic acid sequences. A specific aspect of the present invention is that amplification and monitoring of the amplification process can be made simultaneously without changing the position of the cartridge. A further aspect of this invention is the complete and bubble free filling of cartridges with fluids for thermocycling. The monitoring of the amplification process may be used to quantify the starting concentration of a target nucleic acid.

An apparatus for performing nucleic acid amplifications in reaction cartridges is known from U.S. Pat. No. 5,567,617. This U.S. patent is concerned with an invention for nucleic acid amplification in a flexible cuvette. For amplification this cuvette is placed within a heater having a thin heating element with a central window providing an optical passage. Such an embodiment has the disadvantage that heating and detection compete for free space in the lateral direction of the reaction cuvette. A further problem of the system used in U.S. Pat. No. 5,567,617 is the flexible nature of the cuvette with fluid channels therein. Measures have to be taken to ensure that fluid communication within the cuvette is not obstructed when the cuvette is placed within the heater.

The present invention is directed to a system for thermocycling similar to the system described in U.S. Pat. No. 5,567,617 but having the advantage that heating efficiency is not limited by free space needed for detection. A further advantage compared to U.S. Pat. No. 5,567,617 is that a constriction of fluid passways within the cartridge is uncritical.

Document WO 98/38487 describes an assembly with a thermal sleeve for controlling the temperature within a fluid chamber. The assembly further comprises an optics for interrogation of the chamber content while the chamber is placed in the thermal sleeve.

The chamber disclosed however is designed to receive fluid by bottom up filling via a fluid port at the upper end of the chamber. Filling of such a chamber is uncritical if the inner diameter is large enough to allow fluid to enter without enclosure of air bubbles. Reduction of the diameter, however, is desirable to reduce for the internal distance between temperature controlled walls to allow for sufficient heating and cooling rates of the fluid.

The aim of the present invention is to provide a system for rapid thermocycling of fluids in cartridges with on-line optical monitoring. A particular goal is to achieve rapid heating and cooling rates while avoiding the disturbance of optical measurements by bubbles enclosed in the fluid.

This goal is achieved by a system with a thermocycling unit, a light source, a light detector, a fluid providing unit, and a cartridge in which thermocycling as well as detection can be conducted while the cartridge remains unchanged in position. Such a system allows thermocycling with on-line optical monitoring. On-line monitoring means optical monitoring while temperature cycling is being performed. Furthermore the cartridge has a sufficiently small inner diameter between the temperature controlled walls to allow close temperature control of fluid in the cartridge. Filling of the cartridge is advantageously achieved by a flow-through process.

The cartridge of the present invention has the shape of a thin plate. The two opposing larger walls are used for heat transfer and one or more walls substantially vertical thereto are used for transmitting light into the cartridge and for transmitting light to be detected out of the cartridge. This cartridge design ensures that the optical path and the path for heat exchange are spatially separated so that detection and heat transfer do not compete for space. The thickness of the cartridge is preferably in the range of 2.5-5 mm and the area of each wall for heat transfer is preferably in the range of 0.1-4 cm$^2$. Such a cartridge can be made from a body having a bottom wall and upstanding side walls and the body being closed by a top wall to form a close cartridge with a reaction chamber therein. A preferable embodiment of the cartridge is however made from a frame which provides the side walls of the cartridge and which is closed by a bottom and a top wall. It is particular preferred when top and bottom walls are foils with a thickness of less than 200 μm. A cartridge in accordance with the present invention may have a uniform thickness but it is however preferred when the heat conducting top and bottom walls form an angle of 3 to 8 degree with respect to each other. Such a wedge shaped cartridge has the advantage that it provides efficient heat transfer and easy handling when used in connection with a thermocycling unit having a receiving section of a respective wedge shape.

Cartridges of the present invention can be made from transparent plastics. Preferably an annular shaped frame with a wall thickness of 0.3-4 mm is provided to form the side walls of the cartridge. The frame can be made e.g. by injection molding from polymers as polyethylen or polypropylen. The frame is closed by foils forming top and bottom walls by heat sealing. Processes for sealing a polymer foil onto such a frame are well known in the art and will therefor not be discussed in detail herein. Heat sealing processes are e.g. described in: Polymere Werkstoffe: 3rd volume, Editor: Hans Batzer. Stuttgart; New York: Thieme. Bd. 2. Technologie 1, 1984, pages 206-212; Kunststoffverarbeitung; Editor: Otto Schwarz et al.; 4th revised edition Würzburg: Vogel, 1988, pages 193-206 and Kunststoff-Folien: Herstellung, Eigenschaften, Anwendung; Editor: Joachim Nentwig. München, Wien: Hanser, 1994, pages 88-93. Metallised multilayer foils can also be employed for sealing onto the frame.

As will become clearer below in connection with the filling process the cartridge is being made from materials with high surface tension or the surface tension of inner walls can be enhanced. Such an enhancement of surface tension can be achieved by adequate oxid coating or plasma treatment of the surface. The limiting surface tension value enabling bubble free filling, however, depends on the surface tension of the fluid.

As mentioned it is advantageous to employ cartridges with a small internal diameter between the heat controlled walls of the cartridge. It has shown that a diameter below approx. 5 mm allows close temperature control and thus high heating and cooling rates.

It should be noted that the interior of the cartridge may have fluid channels, as well as protrusions and recesses. Furthermore the used language "closed cartridge" does not exclude fluid channels intersecting the walls of the cartridge which are used for bringing fluids into or out of the cartridge.

The thermocycling unit of the present invention comprises a heating section for establishing a thermal contact with the heat conducting walls of the cartridge. The heating section preferably comprises at least one plate which is brought into mechanical contact with the heat conducting wall of the cartridge and the plate itself being heated and cooled as necessary for the thermocycling process. This heating and cooling can be made by e.g. Peltier elements, bringing the plate into contact with hot and cold fluids or by heating with a resistor heater and cooling by blowing air onto the plate. Procedures and apparatuses for performing thermocycling by thermal contact with plates are well known in the art.

It should be understood, however, that other devices for heating and cooling the cartridges can be used without departing from the scope of the invention. It is only necessary that whatever device is used for heating and cooling the cartridges, be capable of reaching and sustaining the temperatures involved and achieve the desired temperature versus time profile. Thus, for purposes of nucleic acid amplification, such a device should be capable of cycling the temperature of the amplification reaction mixture between a denaturing temperature $T_1$ (which can be in the range of about 80-105° C. and preferably 90-100° C.) and an annealing/extension temperature $T_2$ (which can be in the range of about 30-90° C. and preferably 50-70° C.) where $T_1 > T_2$ as is known to those skilled in the art.

To achieve a sufficient thermal contact between the cartridge and the heating section means can be provided which press one or two plates against the cartridge. Such means are e.g. described in U.S. Pat. No. 5,567,617. In the context of the present invention it is however preferred to employ a heating unit having a receiving section of a wedge shaped recess. The receiving section may be formed by two walls which are inclined one to the other. A wedge shaped cartridge can be simply placed into such a wedge shaped receiving section and sufficient thermal contact between the walls of the receiving section and the heat conducting walls of the cartridge is automatically achieved by mechanical contact into which the respective walls come when the cartridge runs down into the receiving section.

The thermocycling unit further comprises a steering unit which steers the timely heating and cooling of the heater section. Such a steering section is for example described in EP B 0 236 069 which is hereby incorporated by reference. The present invention does not need a steering unit different to the one described in EP B 0 236 069 but timing, temperature profiles and the amount of heat exchanged with the cartridge has to be adapted to the specific needs.

The present invention involves nucleic acid amplification and the detection, monitoring and quantification of amplification products. In order to facilitate understanding of the amplification data collection and processing system of the present invention, a summary of nucleic acid amplification processes especially suited for use in conjunction with the invention will first be discussed.

Those of skill will recognize that the present invention requires amplification of the duplex form of nucleic acid. There exist well-known methods for amplifying nucleic acids. The means for amplification are not critical and this invention will work with any method where nucleic acid duplexes are generated. The various methods are reviewed in Bio/Technology 8:290-293, April 1990. They include, but are not limited to PCR, LCR, Qβ and 3SR. Although 3SR and Qβ do not involve thermal cycling, the result of their amplifications can be monitored by the fluorescence detecting arrangement discussed below and analyzed in accordance with the principles of the present invention. Each method is briefly described below.

PCR amplification of DNA involves repeated cycles of heat denaturing the DNA, annealing two oligonucleotide primers to sequences that flank the DNA segment to be amplified, and extending the annealed primers with DNA polymerase. The primers hybridize to opposite stands of the target sequence and are oriented so that DNA synthesis by the polymerase proceeds across the regions between the primers, each successive cycle essentially doubling the amount of DNA synthesized in the previous cycle. This results in the exponential accumulation of the specific target fragment at a rate of approximately $2^n$ per cycle, where n is the number of cycles. A complete review of this technology can be found in PCR Technology—Principles and Applications, Ed. Erlich H. A., Stockton Press, Now York 1989. Taq DNA polymerase is preferred when PCR is used in conjunction with the present invention although this is not an essential aspect of the invention.

The ligase chain reaction is described in International Patent Application WO 89/09835. The process involves the use of ligase to join oligonucleotide segments that anneal to the target nucleic acid. Ligase chain reaction (LCR) results in amplification of an original target molecule and can provide millions of copies of product DNA. Consequently, the LCR results in a net increase in double-stranded DNA. The present detection methods are applicable to LCR, as well as PCR LCR typically requires some means for detecting the product DNA such as an oligonucleotide probe. When used in conjunction with the disclosed methods for detecting amplification products, such means are unnecessary, and the LCR result is immediately detectable.

Another amplification scheme, Q-beta replicase, exploits the use of the replicase from the RNA bacteriophage Qβ. In this amplification scheme, a modified recombinant bacteriophage genome with a sequence specific for the targeted sequence is initially ligated to the nucleic acid to be tested. Following enrichment of the duplexes formed between the bacteriophage probe and the nucleic acid in a sample, Qβ replicase is added, which, upon recognizing the retained recombinant genome, begins making a large number of copies. The Qβ system does not require primer sequences and there is no heat denaturation step as with the PCR and LCR amplification systems. The reaction occurs at one temperature, typically 37° C. The preferred template is a substrate for the Qβ replicase, midvariant-1 RNA. A very large increase in the templates is achieved through the use of this system. A review of this amplification system can be found in International Patent Application WO 87/06270 and in Lizardi et al., 1988, Bio/Technology 6:1197-1202.

The 3 SR system is a variation of an in vitro transcription-based amplification system. A transcription-based amplification system (TAS) involves the use of primers that encode a promoter sequence as well as a complementary sequence to the target strand to generate DNA copies of a target strand and the production of RNA copies from the DNA copies with an RNA polymerase. See, e.g., Example 9B of U.S. Pat. No. 4,683,202 and European Patent Application EP-A-0 310,229. The 3SR System is a system which uses three enzymes to carry out an isothermal replication of target nucleic acids.

The system begins with a target of singlestranded RNA to which a T7 RNA DNA primer is bound. By extension of the primer with reverse transcriptase, a cDNA is formed, and RNAseH treatment frees the cDNA from the heteroduplex. A second primer is bound to the cDNA and a doublestranded cDNA is formed by reverse transcriptase treatment. One (or both) of the primers encodes a promoter, e.g., the promoter for T7 RNA polymerase, so that the double-stranded cDNA is a transcription template for RNA polymerase.

Transcription competent cDNAs yield antisense RNA copies of the original target. The transcripts are then converted by the reverse transcriptase to double-stranded cDNA containing double-stranded promoters, optionally on both ends in an inverted repeat orientation. These DNAs can yield RNAS, which can reenter the cycle, A more complete description of the 3SR system can be found in Guatelli et al., 1990, Proc. Natl. Acad. Sci. USA 87:1874-1878, and European Patent Application EP-A-0 329 822.

According to the present invention, nucleic acid amplification is monitored by detecting fluorescence emitted when a fluorescent dye such as an intercalating fluorescent dye, provided in the reaction mixture, binds with the double-stranded nucleic acid during each annealing/extension phase as the mixture is cycled between two temperatures (thermal cycling). An increase in fluorescence indicates a positive amplification of target nucleic acid. Suitable intercalating agents or dyes include, but are not limited to ethidium bromide, propidium bromide, proflavine, acridine orange, acriflavine, fluorcoumarine, ellipticine, daunomycin, chloroquine, distamycin D, chromomycin, homidium, mithramycin, ruthenium polypyridyls, anthramycin, methidium bromide, 2-[2-(4-hydroxyphenyl)-6-benzimidazole-6-(1-methyl-4-piperazye) benzimidazole trihydrochloride and the like.

Fluorophores and DNA binding chromophores described in the art are suitable for use in the 5' to 3' nuclease assay disclosed in U.S. Pat. No. 5,210,015 are also useful in the present invention. Suitable donor fluorophores and quenchers are chosen such that the emission spectrum of the donor fluorophore overlaps with the absorption spectrum of the quencher. Ideally, the fluorophores should have a high Stokes shift (a large difference between the wavelength for maximum absorption and the wavelength for maximum emission) to minimize interference by scattered excitation light.

Suitable labels which are well known in the art include, but are not limited to, fluoroscein and derivatives such as FAM, HEX, TET, and JOE; rhodamine and derivatives such as Texas Red, ROX, and TAMRA; Lucifer Yellow, and coumarin derivatives such as 7-Me2N-coumarin-4-acetate, 7OH-4-CH3-coumarin-3-acetate, and 7-NH2-4-CH3coumarin-3-acetate (AMCA). FAM, HEX, TET, JOE, ROX, and TAMRA are marketed by Perkin Elmer, Applied Biosystems Division (Foster City, Calif.). TEX-as Red and many other suitable compounds are marketed by Molecular Probes (Eugene, Oreg.). Examples of chemiluminescent and bioluminescent compounds that may be suitable for use as the energy donor include luminol (aminophthal-hydrazide) and derivatives, and Luciferases.

The optics of a system in accordance with the present invention comprises a light source and a light detector. With the system absorption or scattering measurements with the fluid within the cartridge can be performed. It is however preferred to use this system for fluorescent measurements where light is transmitted into the interior of the cartridge to initiate fluorescence emission which is detected by the light detector. The light source may comprise semi-conductor light sources as well as halogen lamps or other embodiments. Within the spirit of the present invention the light is transmitted into the cartridge through a second light transparent wall of the cartridge which is substantially perpendicular to the wall for heat transfer. Due to the flat shape of the cartridge the second light transparent wall has a width of only 0.5 to 5 mm in one dimension. It is therefor preferred to employ beam shaping optics cooperating with the light source to introduce light through this restricted window. Such beam shaping optics may include apertures, lenses and fibre optics. For fluorescent measurements it is necessary to stimulate fluorescent dyes with light of a wavelength within the absorption spectrum of the dye. It is normally desired to suppress background radiation caused by light emission from other sources than the fluorescent dye. In many embodiments it is furthermore desirable to perform fluorescent measurements with two or more dyes within the same reaction volume. In these cases it is necessary to restrict the bandwidth of the light for illumination. This can be done by using light sources having a narrow bandwidth as for e.g. LED's or by using light sources having a broad bandwidth in connection with suitable filters.

A system of the present invention further comprises one or more light detectors for detecting light emerging from the interior of the cartridge through the second light transparent wall. Suitable light detectors are semiconductor detectors as photodiodes or photomultipliers. As already mentioned it is desirable to suppress background signals and therefore detection should be limited to the emission band of the fluorescent dye to be detected. This can be achieved by wavelength filters or by spectral separation of the light with a spectrometer. Within the present invention it is preferred to detect two or more fluorescent dyes within the same cartridge by separate detection of the emitted fluorescent radiation from the dyes. Advantageously the dyes are also stimulated separately with suitable light sources.

The light detector of the present invention may cooperate with light directing means as fibreoptics, lens systems and so on.

The cartridge of the present invention is used as a thermocycling cavity for fluids and it therefore has an inlet for providing the cartridge with fluid. Optionally the cartridge may have an outlet for draining fluid from the cartridge. It is however preferred in some modes of use to have a disposable cartridge without an outlet for liquid. Such a cartridge can be discarded together with its content after use. The inlet and the optional outlet are preferably channels through the body or through the frame of the cartridge. As already mentioned body or flame are made mostly incompressible so that the fluid channels are not obstructed when pressure is applied to the cartridge in order to achieve a thermal contact with the heating unit. A system in accordance with the present invention comprises a fluid providing unit which is coupled to the inlet of the cartridge. Such a fluid providing unit may be a pipetting unit or an internal fluid channel of the system from which fluid is pressed into the cartridge. The system optionally comprises a fluid receiving unit which is coupled to an outlet of the cartridge to receive fluid from the cartridge. Such a fluid receiving unit is necessary if the cartridge has to be emptied or if different fluids have to be processed within the same cartridge. In preferred embodiments the cartridge is however discarded together with the fluid therein after single use. Such embodiments do not need a fluid receiving unit but only an outlet to drain gas when the cartridge is filled with fluid.

Cartridges in accordance with the present invention a preferably filled by the so called flow-through-filling. Flow-through filling means that fluid is introduced via an inlet and fills the inner space of the cartridge directly adjacent the inlet. Introduction of further liquid continuously enlarges the filled space until a desired degree of filling is achieved. In this process the fluid bolus is never released from the inlet during filling as it is the case for bottom-to-top-filling as described in WO 98/38487. To allow for a flow-through-filling process the inner geometry of the cartridge, respectively the channel connecting inlet and outlet is important. For thermocycling cartridges it is desirable to have a large contact area of fluid with the thermally controlled walls. The dimension of the channel which controls the contact area will be denoted $D_L$ (lateral diameter) and the internal distance between the thermally controlled walls $D_V$ (vertical diameter). The larger the quotient $D_L/D_V$ the more efficient is heat control as well as the risk that bubbles are enclosed during filling. It has shown that optimal quotients $D_L/D_V$ are in the range of 1 to 10.

Bearing in mind that the risk of bubble formation increases with increasing lateral diameter the quotient should be calculated employing the largest vertical diameter (Dv, max) of the channel, wherein the diameter is measured vertical to the flow direction.

Other factors as surface tension (of wall and fluid), viscosity of the fluid, capillary forces and filling rate also will influence the filling process. Said fluid channel, however does not necessarily have a unique shape at each section. It has shown advantageous to employ a curved channel so that the length L of the channel is larger than the geometric distance D between inlet and outlet. Such a design can efficiently be generated by a protrusion projecting into the interior of the cartridge as shown in FIG. 1.

The cartridge may also have a space for receiving gases which are set free during heating of the fluid. This space is arranged in a section of the cartridge which does not interfere with optical measurement.

The present invention is further described in more detail with the regard to the following figures:

FIG. 1: Cartridge in top view partially filled with fluid

Figure 2:
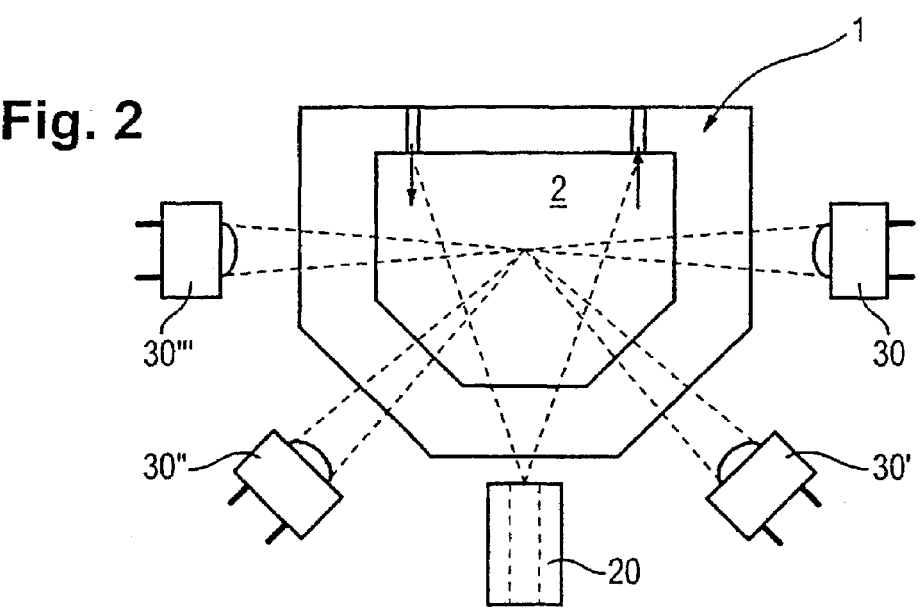

FIG. 2: Cartridge in top view with light sources and detector

Figure 3:
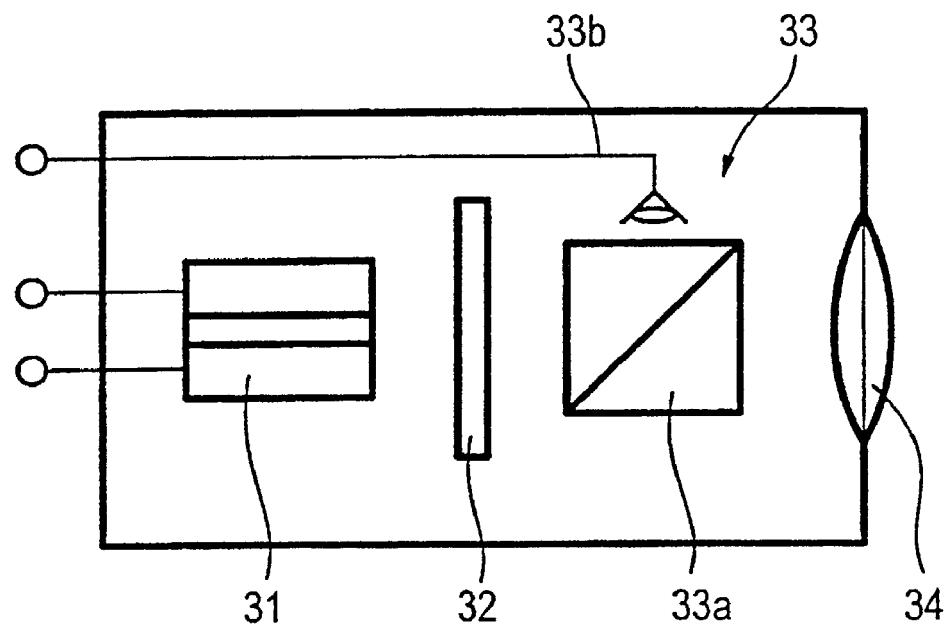

FIG. 3: Light source module

Figure 4:
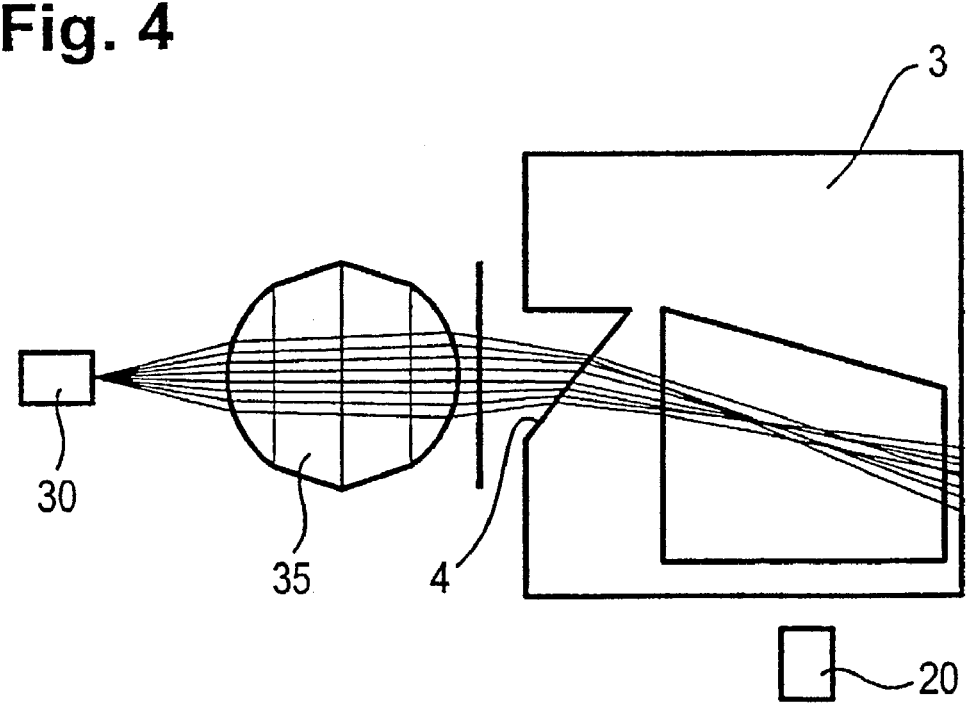

FIG. 4: Raytrace diagram with cartridge having an oblique window

Figure 5:
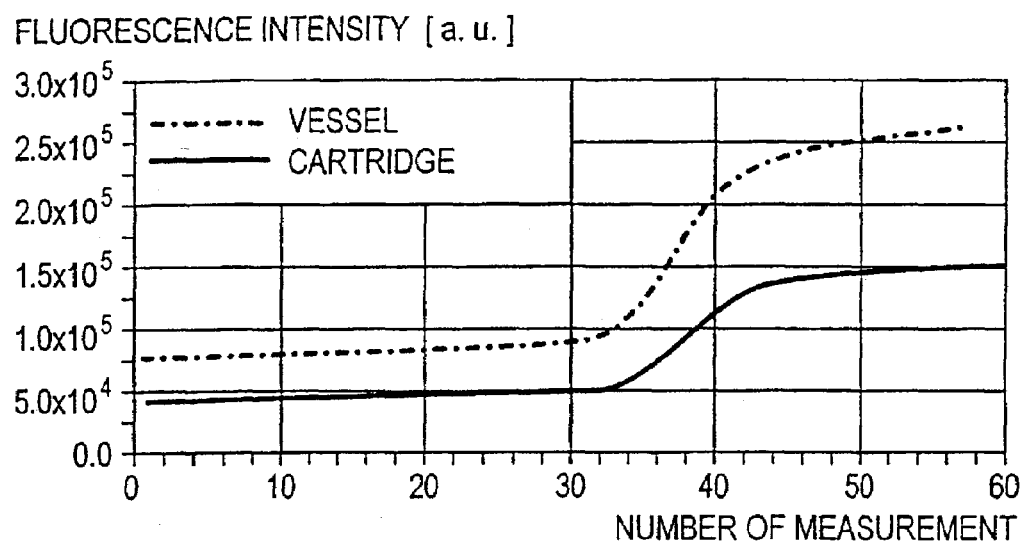

FIG. 5: Fluorescence signal during thermocycling

Figure 6:
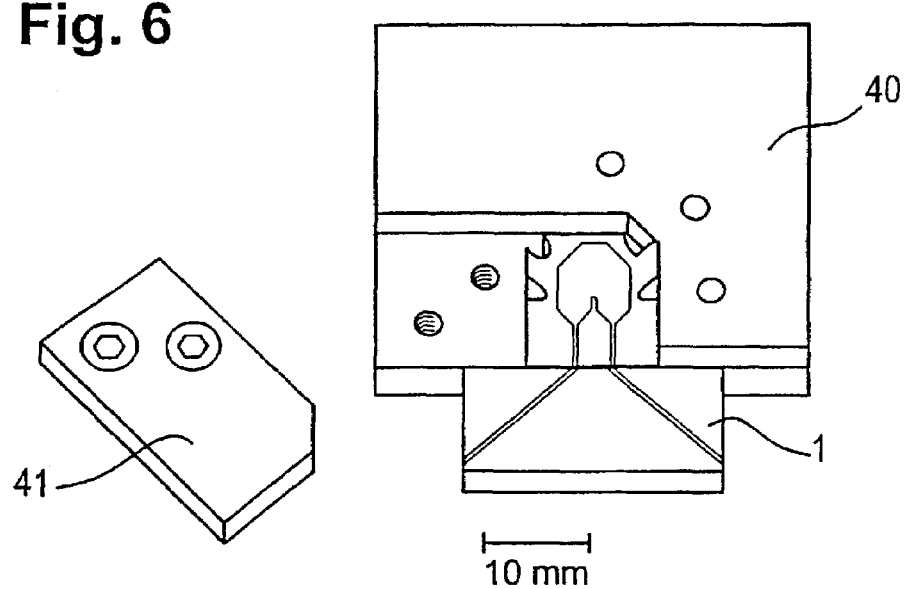

FIG. 6: System for thermocycling in a cartridge within a metal block thermocycler, integrating light sources and light detector.

Figure 7:
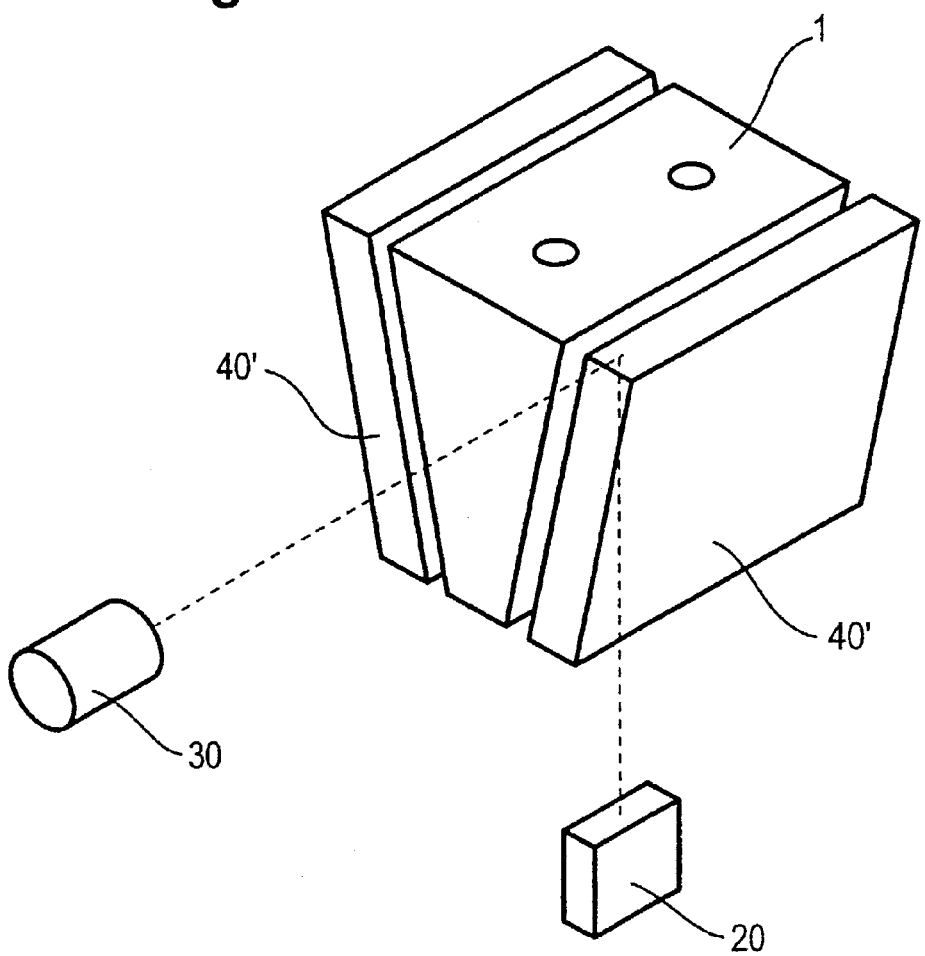

FIG. 7: System for thermocycling with wedge shaped cartridge

Figure 8:
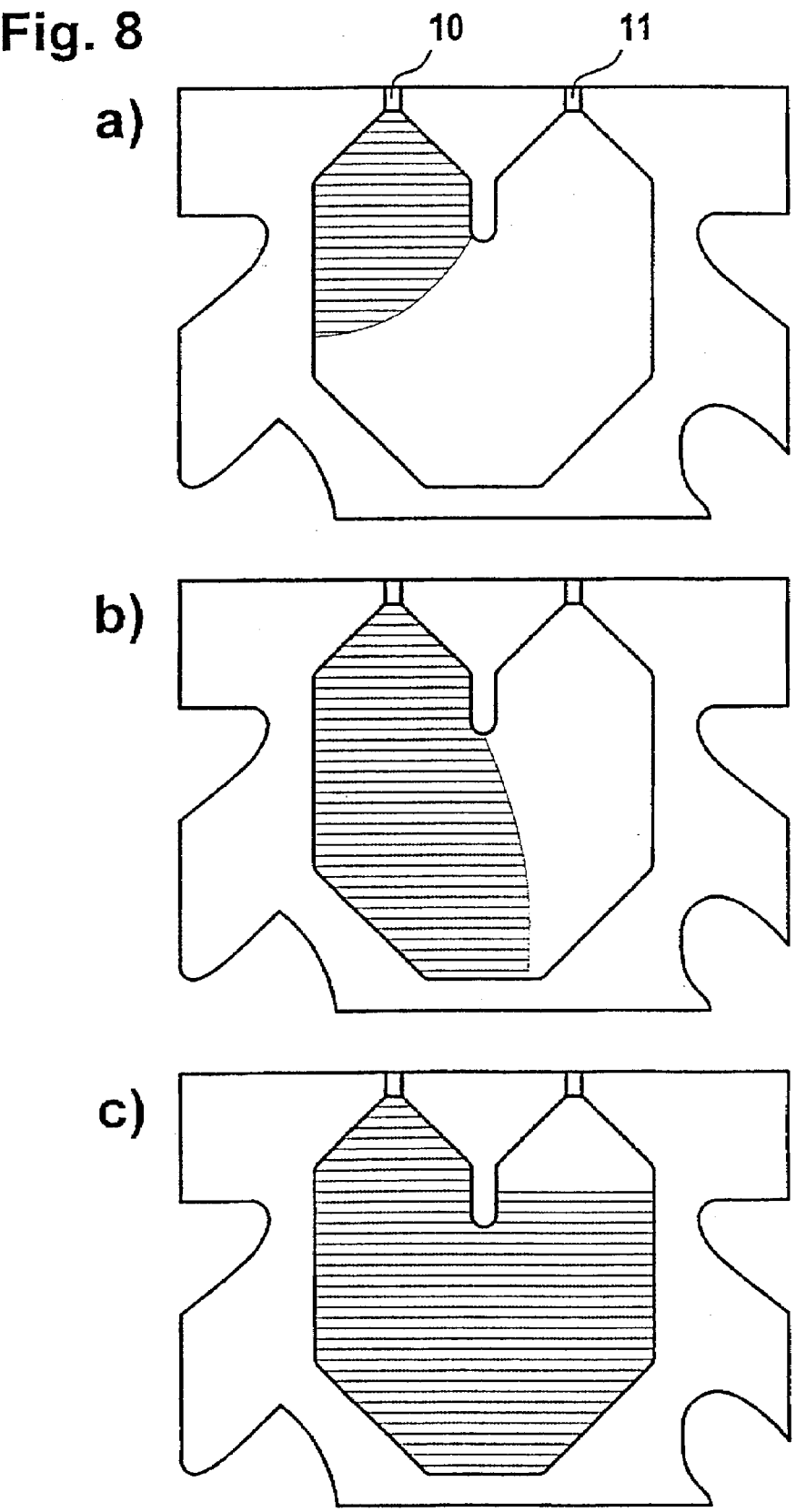

FIG. 8: Filling process of cartridge shown in FIG. 1.

FIG. 1 shows a cartridge (1) for thermocycling of fluids in top view. The cartridge has a body (3) with a cavity (2) therein. The cartridge body has been molten from a solid polypropylene block. In the region of the cavity material was removed until a cell bottom of 200 μm thickness had been achieved. (In serial production the cartridge can be produced more efficiently by injection molding.) Into the polypropylene block has also been molten an inlet (10) to receive fluid and an outlet (11) to vent air from the cavity during filling. The body of the cartridge shown in FIG. 1 has been closed by welding a sealing foil of 40 μm thickness onto the cartridge body. FIG. 1 shows a preferred shape of the cavity (2) with a protrusion (5) in form of a nose reaching into the cavity. The protrusion (5) ensures that the cavity can be filled completely with fluid without enclosure of air bubbles.

The protrusion modifies the geometry of the cartridge so that the largest lateral diameter $D_{L, max}$ is reduced as well as the quotient $D_{L, max}/D_V$ ($D_v$ is the distance between the heat controlled walls; i.e. the thickness of the fluid in the cartridge). In the shown experimental setup $D_{L, max}$ was 4.0 mm and $D_V$ was 1.5 mm resulting in a quotient of 2.7.

The size of protrusion (S) has to be adapted to this specific situation and depends on cavity thickness, viscosity of the liquid, surface tension of bottom and top wall of the cartridge as well as size and shape of the cavity. It has been found that the effect of the protrusion is to avoid a fluidic shortcut between inlet and outlet. In this spirit the protrusion directs the fluid on a path (L) which is longer than the shortest distance (D) between inlet and outlet. In FIG. 1 there have been shown several fluid paths by dotted lines. It has been found to be advantageous if the quotient of the shortest L divided by D is two or more. FIG. 1 furthermore shows a preferred embodiment with respect to the location of inlet and outlet on the same side of the cartridge. With this arrangement it is possible to locate fluid connections on the same side and make connection to an apparatus easier. A disposal of inlet and outlet on the same side is also advantageous in that this side may be located upside within the system during filling, cycling and measurement. By this arrangement air bubbles remaining occasionally in the cavity or being created during heating of the cartridge can be eliminated through the inlet or the outlet port. FIG. 1 also shows an advantageous shape of the cavity adjacent inlet and outlet. As can be seen the walls, (7, 7', 7", 7''') form an angle with the inlet and outlet of approximately 130°. A preferred range of this angle is 100-150° which has shown to avoid empty spots when filling the cavity with fluid. A further aspect of the present invention which can be seen in FIG. 1 are the oblique windows (4, 4'). Light is irradiated into the cavity perpendicular to surfaces (8, 8') of the cavity and is detected by schematically shown detector (20). The irradiating light is being refracted by the oblique surfaces (4, 4') in a direction towards the detector. Due to this arrangement the generation of fluorescent light can be directed to a central portion of the cavity which is closer to the detector in order to increase the measurement sensitivity.

FIG. 2 shows a schematic drawing of a cartridge in combination with light sources (30, 30', 30", 30''') and a detector (20). As can be seen the focal point of the light sources is being disposed in the centre of the cavity and the focal points are mostly coincident. The detector (20) is disposed beneath the detection window of the cartridge to detect fluorescent light from the centre of the cavity. With the setup of FIG. 2 it is possible to monitor the fluorescence of four different fluorescent dyes. Each of the light sources is chosen to specifically stimulate one of the fluorescent dyes. By subsequent activation of the light sources the amount of each fluorescent dye can be monitored by detection of fluorescent radiation with the detector.

FIG. 3 shows a light source module which can be advantageously used within the present invention. The light source module comprises a semiconductor light source (31) a wavelength selection filter (32) and an optical output power monitor (33). The output power monitor comprises a beam splitter (33a) to extract a portion of the light from the light path and a detector (33b) to detect the extracted light. The amount of light detected is used to steer the current applied to the semiconductor light source so as to generate a constant and specific output. The light source module of FIG. 3 further comprises a beam shaper (34) in form of a lens. Advantageously the light emitting surface of the semiconductor light source is imaged by the lens into the centre of the cartridge.

FIG. 4 shows a raytrace of a system employing a cartridge with an oblique window. As can be seen the light generated by light source (30) is imaged by a ballshape lens (35) onto an oblique window (4) of the cartridge. Due to this rangement the light is refracted in direction of the detector (20).

FIG. 5 depicts a fluorescence over time diagram which was measured with the system according to the present invention. The abscissa shows the number of the measurement and the ordinate shows fluorescence intensity in arbitrary units. Measurements were taken after each denaturation, elongation cycle of the polymerase chain reaction. A cartridge (1) as shown in FIGS. 1 and 6 has been introduced and fixed in a holder as shown in FIG. 6.

The holder with the cartridge had been integrated into a thermocycler unit. Illumination optics with simple beam shaping optics and detection optics have been used for quantitative fluorescence measurement. PCR runs (HCV-control with Mastermix, $5\times10^3$ initial copies) with the following protocol have then been performed: 120 cycles, denaturation temperature $T_{denat}=94°$ C., annealing temperature $T_{anneal}=60°$ C., temperature ramp time $t_{ramp}$ approx. 20 s, temperature plateau $t_{plateau}$ approx. 26 s, total process time $t_{tot}$ approx. 3 h. The experimentally measured fluorescence signal vs. number of measurement is plotted in FIG. 5 (solid line). For comparison, the fluorescence signal of an amplification within a vessel has been measured with the same PCR protocol. The result is also shown in FIG. 5 (dotted line). The decreased fluorescence signal of the cartridge (approx. factor 2) is a result of the beam shaping optics used for measurement. This optics introduces an illumination power loss of approximately 30%.

FIG. 6 shows a cartridge of the present invention in the cavity of a metal block for thermocycling. Within the metal block there are integrated light sources and a light detector. For thermocycling the closure (41) can be screwed onto the metal block (40) so as to achieve an optimum thermal contact between the cartridge and the metal block. The metal block itself is provided with Peltier elements for heating and cooling.

FIG. 7 shows an advantageous system in accordance with the present invention. The cartridge shown is a wedge shaped embodiment having a larger thickness on the side of inlet and outlet. The system is provided with a wedge shaped receiving unit comprising of Peltier elements (40') forming an angle one to the other so as to receive the wedge shaped cartridge. With this embodiment it is possible to achieve an intensive thermal contact between the cartridge and the heating unit by simply inserting the cartridge between the Peltier elements (40'). This figure shows that the optical path and the path for heat exchange are spatially separated so that detection and heat transfer do not compete for space.

FIG. 8 shows the filling of the cartridge of FIG. 1 with fluid. Fluid is introduced through inlet (10) and fills the cartridge region directly adjacent the inlet (picture a)). Further introduction of fluid enlarges the filled region as can be seen in FIGS. 8b) and c). This flow-through-filling process provides a bubble free filling of the cartridge.

The invention claimed is:

1. A system for thermocycling of fluids in cartridges comprising
   a) a cartridge with at least one heat conducting wall and at least one light transparent wall, the cartridge having a fluid inlet and a fluid outlet which are connected by a channel, said cartridge having a protrusion into the channel, such that the channel is longer than the shortest distance between the fluid inlet and the fluid outlet to allow bubble-free flow-through filling of the cartridge, wherein the fluid inlet is directly connected to a top wall, a bottom wall, and a pair of sidewalls, wherein the side walls form an angle of 100°-150° with the walls of the fluid inlet, and wherein the fluid outlet is directly connected to the top wall, the bottom wall, and a pair of side walls, wherein the side walls form an angle of 100°-150° with the walls of the fluid outlet,
   b) a thermocycling unit in thermal contact with said heat conducting wall of said cartridge,
   c) a light source for transmitting light into the interior of said cartridge through said light transparent wall of said cartridge which is arranged substantially perpendicular to said heat conducting wall,
   d) a light detector for detecting light emerging from the interior of the cartridge through said light transparent wall,
   e) a fluid providing unit coupled to an inlet of the cartridge for providing the cartridge with fluid by flow-through-filling.

2. The system of claim 1, wherein the cartridge has a body comprising the light transparent wall and having at least one opening which is sealed by a foil providing said heat conducting wall.

3. The system of claim 2, wherein the body is a frame which is sealed by two foils providing heat conducting walls.

4. The system of claim 1 for conducting fluorescent measurements wherein the light detector detects fluorescent light emerging from the cartridge.

5. The system of claim 1, wherein the thermocycling unit comprises at least one plate in thermal contact with the heat conducting wall of the cartridge.

6. The system of claim 1, wherein the cartridge is wedge shaped and the thermocycling unit comprises a wedge shaped receiving section for receiving said wedge shaped cartridge.

7. The system of claim 6, wherein the opposing walls forming the wedge shaped cartridge comprise a top wall, and a bottom wall having an angle of 3° to 8° with respect to each other.

8. The system of claim 1, wherein said light transparent wall comprises a first section through which light is passed from the light source into the cartridge and a second section through which light is passed from the interior of the cartridge onto the light detector.

9. The system of claim 8, wherein said first section is tilted with respect to the illumination beam axis so that the light is refracted towards the second section of said transparent wall.

10. The system of claim 1 or 5, wherein said thermocycling unit comprises a plate in thermal contact with said heat conducting wall of the cartridge and which exerts pressure onto said wall.

11. The system of claim 1, wherein the quotient of the maximal width of said channel and the depth of said channel is in the range of 1 to 10.

12. The system of claim 1 or 11, wherein the depth of the channel is in the range of 0.5 to 5 mm.

13. A method for thermocycling of fluids employing a system according to claim 1, comprising the steps of filling the cartridge by a flow-through-process avoiding bubbles in a measuring section of the cartridge, thermal cycling of fluid in the cartridge, transmitting light into the cartridge and detecting light emerging the cartridge.

14. The method of claim 13 additionally comprising monitoring the light emerging the cartridge to monitor amplification of nucleic acids in the fluid during thermal cycling.

15. A cartridge for conducting thermal cycling of fluids, comprising
   a) a substantially planar and heat conducting wall,
   b) a light transparent wall which is disposed substantially vertical to said heat conducting wall,
   c) a fluid inlet for providing the cartridge with fluid,
   d) a fluid outlet for draining fluid or gas from the cartridge,
   e) a channel connecting the fluid inlet and the fluid outlet, wherein said cartridge has a protrusion, into the channel, such that the channel between the fluid inlet and the fluid outlet is longer than the shortest distance between the fluid inlet and the fluid outlet to allow flow-through-filling of the cartridge to avoid bubbles in a measuring section of the cartridge, wherein the fluid inlet is directly connected to a top wall, a bottom wall, and a pair of side walls, wherein the side walls form an angle of 100°-150° with the walls of the fluid inlet, and wherein the fluid outlet is directly connected to the top wall, the bottom wall, and a pair of side walls, wherein the side walls form an angle of 100°-150° with the walls of the fluid outlet.

16. The cartridge of claim 15, wherein the top wall and the bottom wall are opposing heat conducting walls.

17. The cartridge of claim 15 or 16, wherein the heat conducting wall is a foil with a thickness of less than 200 μm.

18. The cartridge of claim 15 or 16, having opposing top and bottom walls from which at least one is a heat conducting wall and which form an angle of 3° to 8° with respect to each other.

19. The cartridge of claim 15, wherein the light transparent wall comprises a first section for transmitting light into the cartridge and a second section for transmitting light emerging from the cartridge.

20. The cartridge of claim 15, which is made from a body having at least one opening which is closed by a heat conducting foil.

21. The cartridge of claim 15, which is made from a frame which is closed by two opposing foils.

22. The cartridge of claim 15 having a thickness of 0.5 to 5 mm.

23. The cartridge of claim 15, wherein the quotient of the maximal width of said channel and the depth of said channel is in the range of 1 to 10.

24. The cartridge of claim 23, wherein the depth of the channel is in the range of 0.5 to 5 mm.

* * * * *